United States Patent [19]

Bálint et al.

[11] Patent Number: 4,668,274
[45] Date of Patent: May 26, 1987

[54] ETHERIFIED 2-HYDROXY-ETHYL-PHOSPHONIC ACID DERIVATIVES AND PLANT GROWTH REGULATING AGENTS CONTAINING SAME AS ACTIVE INGREDIENT

[75] Inventors: Sándor Bálint, Veszprém; Judit Benczik née Pásztor, Balatonalmádi; József Fodor, Veszprém; András Horváth, Balatonfüzfo-gyártelep; Elemér Tömördi; Csaba Söptei, both of Veszprém; József Karsai, Velence; Endre Sebestyén, Agárd; Sándor Gaál, Szigethalom; Iván Gárdi, Budapest; György Kiss, both of Budapest; Andráss Papp, Törökbálint; Imre Csatlós, Hódmezovásárhely all of Hungary

[73] Assignee: Nitrokémia Ipartelepek, Füzfögyártelep, Hungary

[21] Appl. No.: 839,499

[22] PCT Filed: Jul. 17, 1985

[86] PCT No.: PCT/HU85/00044

§ 371 Date: Mar. 13, 1986

§ 102(e) Date: Mar. 13, 1986

[87] PCT Pub. No.: WO86/00904

PCT Pub. Date: Feb. 13, 1986

[30] Foreign Application Priority Data

Jul. 18, 1984 [HU] Hungary .................. 2800/84

[51] Int. Cl.⁴ .................. A01N 57/24; C07F 9/40
[52] U.S. Cl. ........................ 71/86; 549/220
[58] Field of Search ............... 549/220; 71/86

[56] References Cited

U.S. PATENT DOCUMENTS 2,159,364  5/1939  Coleman et al.
4,042,370  8/1977  Trueb .......................... 71/86
4,560,682  12/1985  Horoki et al. ................ 514/100

OTHER PUBLICATIONS

Houben—Weyl, Methoden der Organischen Chemie, vol. 12/1, (1963), p. 437.

*Primary Examiner*—Richard L. Raymond
*Attorney, Agent, or Firm*—Gabriel P. Katona

[57] ABSTRACT

The present invention refers to new etherified hydroxyalkyl phosphonic acid derivatives of the general formula (I)

$$R-O-CH_2-CH_2-P\underset{OR^2}{\overset{O\;\;\;OR^1(Me)}{\underset{\|}{\diagup}}}\qquad (I)$$

wherein
R stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7,yl,
$R^1$ and $R^2$ are the same or different and stand for hydrogen, $C_{1-8}$ alkyl, $C_{1-4}$ halogen-alkyl, $C_{1-4}$ alkoxy-$C_{1-2}$ alkyl, Me stands for a monovalent cation.

The new compounds can be used as active ingredients of plant growth regulating agents.

6 Claims, No Drawings

ETHERIFIED 2-HYDROXY-ETHYL-PHOSPHONIC ACID DERIVATIVES AND PLANT GROWTH REGULATING AGENTS CONTAINING SAME AS ACTIVE INGREDIENT

The invention relates to etherified 2-hydroxy-ethyl-phosphonic acid derivatives and plant growth regulating agents containing same as active ingredient. The invention also provides processes for the preparation of the new compounds and the use thereof.

In HU-PS 160,618 as plant growth regulator 2-methoxy-ethyl-phosphonic acid is disclosed.

In Japanese Patent Publication No. 80.111.494 hydroxy-alkyl phosphonic acids substituted by an aromatic group and esters thereof, e.g. 2-(4-chloro-phenyloxy)-ethyl-phosphonic acid dimethylester are disclosed and the compounds were mentioned as showing pharmaceutical activity.

Papukova et al. disclosed various phenoxy-alkyl-phosphonic acids and esters thereof in Zsurn. Prikl. Him. (Leningrad) 1972 45 (8) 1808-1818. The activity of the compounds was, however, not mentioned.

The present invention refers to new etherified hydroxy-alkyl-phosphonic acid derivatives of the general formula (I)

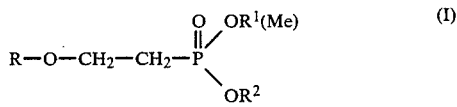

wherein

R stands for 2,3-dihydro-2,2-dimethyl-benzofuran-7-yl-, 4-methyl-coumarin-7-yl, 2,2,4-trimethyl-(2H)-chromen-5-yl, or 2,2,4-trimethyl-(2H)-chromen-7-yl, $R^1$ and $R^2$ are the same or different and stand for hydrogen, $C_{1-8}$ alkyl, $C_{1-4}$ halogenalkyl, $C_{1-4}$ alkoxy-$C_{1-2}$ alkyl and Me stands for a monovalent cation.

The new compounds exhibit plant growth regulating activity.

The plant growth regulating activity according to the invention means that the new compounds act on the physiological process of the plant growth depending on the time of the use, on the development stage of the plant and on the used active ingredient concentration. Due to the properties of the compounds of the invention they can be utilized in agriculture.

The process for the preparation of the new compounds of the general formula (I) can be characterized by reacting 7-hydroxy-2,3-dihydro-2,2-dimethyl-benzofuran or 7-hydroxy-4-methyl-coumarin or 7-(5)-hydroxy-2,2,4-trimethyl-(2H)-chromene with dihaloethane at a temperature ranging from $-10°$ to $+80°$ C. optionally in the presence of a phase transferring catalyst and reacting the obtained intermediate product, if desired after purification with di- or triethyl-phosphite at a temperature ranging from $+40°$ to $+250°$ C. The temperature range is preferably 100° to 200° C. The reaction is illustrated by reaction scheme E where Hal stands for halogen, preferably bromine, $R^1$ represents alkyl, preferably ethyl.

Reaction scheme E

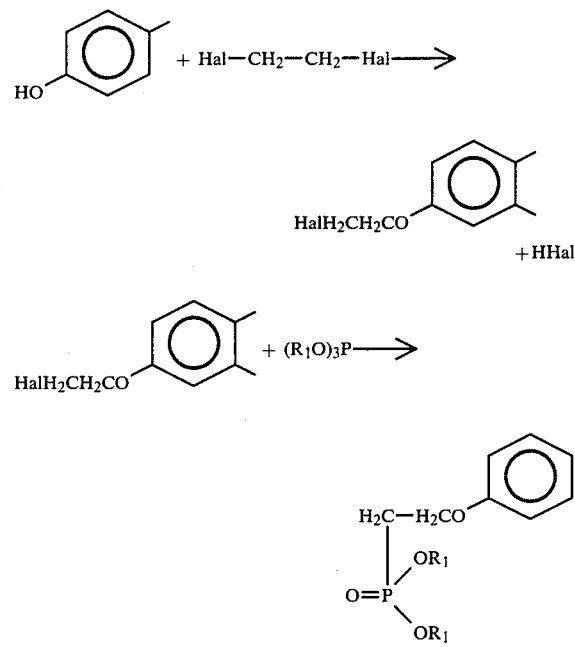

From compounds of the general formula (I) in agriculture acceptable compositions can be prepared by the addition of carriers, optionally surfactants and water soluble concentrates, dusting agents, wettable powders, granules, emulsifiable concentrates or colloidal aqueous suspensions can be prepared.

When preparing these compositions the active ingredients can be admixed with solid or liquid carriers and surfactants and the blend is optionally homogenized.

The compositions contain 0.1-95% by mass active ingredient and the active ingredients can be used in the form of compositions or solutions, emulsifiable concentrates, suspensions, wettable powders, dusting agents and granules ready to use by pouring, spraying or vapourization. The active ingredient concentration can be varied within a wide range depending on the used active ingredient, on the carriers and/or surfactants.

The preparation of the new compounds and the compositions is illustrated in the following Examples.

EXAMPLE 1

Preparation of 2,3-dihydro-2,2-dimethyl-7-(2'-chloro-ethoxy)-benzofuran

To 100 ml. ethylacetate 8.23 g. (0.05 mole) 2,3-dihydro-2,2-dimethyl-7-hydroxy-benzofuran, 14.3 g. (0.1 mole) 1-bromo-2-chloro-ethane, 6.9 g. (0.05 mole) anhydrous sodium carbonate and 8.3 (0.05 mole) potassium iodide are added. The reaction mixture is heated for 30 hours and the reaction is monitored by gas chromatographic analysis.

When the reaction is completed the mixture is cooled to room temperature, the solid is removed by filtration and the solvent is distilled off in vacuo from the solvent layer on a rotatory film evaporator.

The residual yellowish brown oily part is dissolved in 50 ml. methylene chloride and washed with 5×30 ml. 5% sodium-hydroxide solution and water. The solvent part is dried above anhydrous sodium sulphate and the solvent is distilled off on a rotatory film evaporator in vacuo. 5.8 g. yellowish brown liquid are obtained and purified by vacuo distillation. The product distilled at a pressure of 0.2 torr. at 120°–125° C.

EXAMPLE 2

Preparation of 2,3-dihydro-2,2-dimethyl-7-(2'-chloro-ethoxy)-benzofuran

To 200 ml. methylene-chloride 32.84 g. (0.2 mole) 2,3-dihydro-2,2-dimethyl-7-hydroxy-benzofuran, 57.37 g. (0.4 mole) 1-bromo-2-chloro-ethane 200 ml. 2N sodium hydroxide solution and 8 g. Adogen 464 phase transfer catalyst (tri-$C_{8-10}$-alkyl-methyl-ammonium-chloride) are added. The reaction mixture is heated under vigorous stirring for 7 hours and the reaction is monitored by gas chromatographic analysis.

When the reaction is completed the mixture is cooled to room temperature, the methylene-chloride layer is separated from the aqueous layer and washed with 2×50 ml. 2N sodium hydroxide solution, water and then with 2×50 ml. saturated aqueous natrium-chloride solution. The solvent part is dried above anhydrous sodium sulphate and the solvent is distilled off in vacuo on a rotatory film evaporator. The residual pale yellow oily substance weighing 46.1 g. is purified by vacuo distillation and the product distilled at 121°–125° C. at 0.2 torr.

The compounds according to Examples 1 and 2 are used for the further processes.

EXAMPLE 3

Preparation of 2-(2,3-dihydro-2,2-dimethylbenzofuran-7-yl-oxy)-ethyl-phosphonic acid diethylester 68.2 g. (0.3 mole) 2,3-dihydro-2,2-dimethyl-7-(2'-chloro-ethoxy)-benzofuran (prepared according to Examples 1 or 2) and 49.86 g. (0.3 mole) triethylphosphite are stirred at 140°–146° C. for 60 hours and heated. When the reaction is completed the obtained yellowish brown oily product is purified by vacuum distillation by distilling off the volatile contaminations at 0.5 torr. The cuts are collected until 148° C. and the distillation residue is a pure product according to gas chromatographic analysis. The product is a pale yellow oily liquid, $n_D^{24.5}=1.5101$ (compound No. 1).

EXAMPLE 4

(A) Preparation of 2,2,4-trimethyl-7-(2'-bromo-ethyl-oxy)-(2H)-chromene

To a 8% aqueous solution of 0.1 mole (19.02 g.) 2,2,4-trimethyl-7-hydroxy-(2H)-chromene and 0.2 mole (8 g.) sodium hydroxide 4 g. of benzene-tributyl-ammonium-chloride as phase transfer catalyst and a solution of 0.2 mole 1,2-dibromo-ethane in 200 ml. methylene-chloride are added under stirring and the solution is heated for 12 hours. After cooling the organic layer is separated and dried above sodium sulphate and evaporated. The residue is dissolved in 50 ml. diethyl-ether and the substance is precipitated by adding 300 ml. of n-hexane. The solvent is decanted from the precipitated substance. Thus 19.38 g. (0.065 mole) product are obtained in the form of a white waxy oily substance.

(B) Preparation of 2-(2',4',4'-trimethyl-(2H)-chromen-7-yl-oxy)-ethyl-phosphonic acid-iethyl-ester 0.1 mole (29.82 g.) 2,2,4-trimethyl-7-(2'-bromo-ethyl-oxy)-(2H)-chromene and 0.2 mole (33.23 g.) triethylphosphite are heated under stirring for 1 hour. From the obtained reaction mixture the triethylphophite excess and the obtained side product are removed by vacuum distillation and the residual product is a yellowish, thick gume-like substance of a weight of 23.29 g. (0.012 mole), $n_D^{25.1}=1.5962$.

EXAMPLE 5

(A) Preparation of 7-(2'-bromo-ethyl-oxy)-4-methyl-coumarin 17.62 g. (0.1 mole) 7-hydroxy-4-methyl-coumarin (4-methyl-umbelliferon) are dissolved in a 8% aqueous solution of 0.2 mole sodium hydroxide and a solution of 4 g. benzyl-tributyl-ammonium-chloride phase transfer catalyst and 37.5 g. (0.2 mole) 1,2-dibromo-ethane in 200 ml. ethylene-chloride is added. The mixture is heated for 14 hours under stirring and allowed to cool. 60 ml. dichloromethane are added, the mixture is filtered and the organic layer is separated from the filtrate and washed with distilled water, dried and evaporated. 19.82 g. (0.07 mole) 7-(2'-bromo-ethyl-oxy)-4-methyl-coumarin are obtained, melting point: 94°–97° C.

(B) Preparation of 2-(4'-methyl-coumarin-7-yl-oxy)-ethyl-phosphonic acid-O,O-diethylester 28.32 g. (0.1 mole) 7-(2'-bromo-ethyl-oxy)-4-methyl-coumarin and 33.23 g. (0.2 mole) triethylphosphite are heated under stirring for 1 hour. The reaction mixture is then cooled. The end-product is separated from the contaminations by removing same by vacuum distillation. The bottom product is a yellow, thick, oily substance of weight 11.9 g. (0.0035 mole), $n_D^{31}=1.5619$.

According to the process disclosed above the following compounds of the general formula (I) can be prepared.

| Number of Compound | Compound of the general formula (I) R | $R^1$ | $R^2$ | Chemical name |
|---|---|---|---|---|
| 2 | benzofuran-dimethyl structure with O-CH(CH₃)₂ | H | H | 2-(2,3-dihydro-2,2-dimethyl-benzofuran-7-yl-oxy)-ethyl-phosphonic acid |
| 3 | benzofuran-dimethyl structure with O-CH(CH₃)₂ | H | $CH_3$ | 2-(2,3-dihydro-2,2-dimethyl-benzofuran-7-yl-oxy)-ethyl-phosphonic acid-O—methyl-ester |

-continued

| Number of Compound | Compound of the general formula (I) R | R¹ | R² | Chemical name |
|---|---|---|---|---|
| 4 | benzofuran with 2,2-dimethyl | ClCH₂CH₂ | ClCH₂CH₂ | 2-(2,3-dihydro-2,2-dimethyl-benzo-furan-7-yl-oxy)-ethyl-phosphonic acid-bis-(2-chloro-ethyl)-ester |
| 5 | benzofuran with 2,2-dimethyl | CH₃OCH₂CH₂ | CH₃OCH₂CH₂ | 2-(2,3-dihydro-2,2-dimethyl-benzofuran-7-yl-oxy)-ethyl-phosphonic acid-bis(2-methoxy-ethyl)-ester |
| 6 | 2,2,4-trimethyl-2H-chromene (5-yl) | C₂H₅ | C₂H₅ | 2-(2,2,4-trimethyl-(2H)—chromen-5-yl-oxy)-ethyl-phosphonic acid-O,O—di-ethyl-ester |
| 7 | 2,2,4-trimethyl-2H-chromene (7-yl) | C₂H₅ | C₂H₅ | 2-(2,2,4-trimethyl-(2H)—chromen-7-yl-oxy)-ethyl-phosphonic acid-O,O—di-ethyl-ester |

The compounds of the general formula (I) can be converted to liquid or solid compositions by adding formulating excipients such as solid or liquid intert solvents, filling agents and carriers.

The composition of the formulated products is illustrated by the following examples:

EXAMPLE 6

Emulsifiable concentrate

| | |
|---|---|
| Compounds No. 1 | 10% by mass |
| A mixture of poly-oxy-ethylene alkyl-aryl-ether and alkyl-phenol-alkoxalates (Emulsogen I-40, Hoechst) | 7% by mass |
| Xylene | 83% by mass |
| | 100% by mass |

EXAMPLE 7

Emulsifiable concentrate

| | |
|---|---|
| Compound No. 1 | 80% by mass |
| α-[4-(1,1,3,3-tetramethyl-butyl)-phenyl]-ω-hydroxy-poly-(oxy-1,2-ethane (Triton X-100) | 10% by mass |
| Isoferon | 10% by mass |
| | 100% by mass |

EXAMPLE 8

Wettable powder

| | |
|---|---|
| Compound No. 1 | 20% by mass |
| Sodium-oleyl-methyl-tauride (Arkopon T, Hoechst) | 7% by mass |
| magnesium-lignin-sulphonate | 5% by mass |

-continued

| | |
|---|---|
| colloidal synthetic silicondioxide | 28% by mass |
| Kaolin | 40% by mass |
| | 100% by mass |

EXAMPLE 9

Dusting agent

| | |
|---|---|
| Compound No. 1 | 1% by mass |
| Kaolin | 99% by mass |
| | 100% by mass |

EXAMPLE 10

Granule

| | |
|---|---|
| Compound No. 1 | 5% by mass |
| Attapulgit clay | 95% by mass |
| | 100% by mass |

EXAMPLE 11

Emulsifiable concentrate

| | |
|---|---|
| Compound according to Example 5 | 10% by mass |
| Polyoxy-ethylene-sorbitan-monolaurate | 5% by mass |
| ethanol | 85% by mass |
| | 100% by mass |

Biological tests

Etherified 2-hydroxy-ethyl-phosphonic acid derivatives according to the invention and salts thereof were tested for plant growth regulating activity in green house by using tomato, soybean and sunflower as indicating plants. The plants were seeded into pots filled with turf or the plants were grown as seedlings. The post-emergent treatment was carried out on tomatoes at a development stage of 20–30 cm. on soybean and sunflower.

In the course of the tests a control was used and as active ingredient the compound No. 1 i.e. 2-(2,3-dihydro-2,2-dimethyl-benzofuran-7-yl-oxy)-ethyl-phosphonic acid-diethyl-ester and for comparison 2-chloro-ethyl-phosphonic acid ethyl-ester (F) and 2,2-dimethyl-2,3-dihydroxy-7-hydroxy-benzofuran (G) were used. Pre-emergent treatment was carried out with tomato indicating plant, the doses and the obtained results are summarized in tables.

When evaluating the biological tests the change of the height of the plants was established. When carrying out post-emergent treatment in case of tomato the change of height was determined on the 4th, 7th and 10th day after the treatment, on soybean and sunflower and on the 7th day after the treatment and when using pre-emergent treatment the results were determined on the 7th day after the treatment. The data are given in the % of starting plant height.

TABLE 1

Effect of post-emergent treatment on the growth of tomato

| Treatment composition | Dose kg./ha. | Change in the % of the starting height | | |
|---|---|---|---|---|
| | | 4th day | 7th day | 10th day |
| K | | 29 | 53 | 71 |
| Comp. No. 1 | 0.5 | 40 | 75 | 92 |
| | 1.0 | 46 | 80 | 99 |
| | 2.0 | 41 | 68 | 88 |
| F | 0.5 | 42 | 69 | 86 |
| | 1.0 | 41 | 68 | 76 |
| | 2.0 | 43 | 65 | 70 |
| G | 0.5 | 31 | 63 | 78 |
| | 1.0 | 37 | 62 | 80 |
| | 2.0 | 38 | 70 | 83 |

It can be seen that 2-(2,3-dihydro-2,2-dimethyl-benzofuran-7-yl-oxy)-ethyl-phosphonic acid-diethyl-ester significantly increased the growth of tomato related to the untreated control. The activity can be characterized depending on the dose by a curve of second order the peak of which is at the dose of 1 kg./ha. By further increasing the dose the composition already shows a growth reducing effect. It can be further seen that the growth stimulating activity is higher than that of 2,2-dimethyl-2,3-dihydro-7-hydroxy-benzofuran and at higher doses the growth inhibiting activity of latter compound is lower than that of 2-chloro-ethyl-phosphonic acid.

TABLE 2

Effect of post-emergent treatments on the growth of soybean

| Treatment Composition | Dose kg./ha. | Change in the % of the starting height | | | | | |
|---|---|---|---|---|---|---|---|
| | | I. | II. | III. | IV. | V. | Average |
| K | | 23.4 | 26.9 | 21.1 | 25.1 | 26.2 | 24.5 |
| Compo. No. 1 | 0.5 | 16.5 | 15.3 | 16.8 | 15.3 | 16.1 | 16.0 |
| | 1.0 | 15.8 | 13.6 | 16.5 | 16.6 | 14.8 | 15.5 |
| | 2.0 | 14.1 | 14.1 | 15.2 | 15.9 | 15.6 | 15.0 |
| F | 0.5 | 13.0 | 11.3 | 14.1 | 15.1 | 9.4 | 12.6 |
| | 1.0 | 15.1 | 10.6 | 12.4 | 11.4 | 11.4 | 12.2 |
| | 2.0 | 6.6 | 10.0 | 18.5 | 9.5 | 8.8 | 8.7 |
| G | 0.5 | 33.8 | 28.2 | 32.5 | 37.6 | 33.3 | 33.1 |
| | 1.0 | 22.6 | 30.4 | 35.8 | 22.1 | 33.8 | 28.9 |
| | 2.0 | 23.8 | 18.4 | 20.5 | 20.6 | 19.5 | 20.6 |

In soybean the growth reducing activity of 2-(2,3-dihydro-2,2-dimethyl-benzofuran-7-yl-oxy)-ethyl-phosphonic acid-diethyl-ester could be seen independently of the dose. In the effect of the tested doses there was no significant difference. By further increasing the dose no stronger depressive effect could be observed which can be observed for 2-chloro-ethyl-phosphonic acid in case of using an overdosage.

TABLE 3

Effect of post-emergent treatment on the growth of sunflower

| Treatment Composition | Dose kg./ha. | Change in the % of the starting height | | | | | |
|---|---|---|---|---|---|---|---|
| | | I. | II. | III. | IV. | V. | Average |
| K | | 33.0 | 38.8 | 31.1 | 27.9 | 26.7 | 31.5 |
| Comp. No. 1 | 1.0 | 8.6 | 9.1 | 8.8 | 8.8 | 7.9 | 8.6 |
| | 2.0 | 8.1 | 8.8 | 7.4 | 8.6 | 8.5 | 8.2 |
| F | 1.0 | 6.3 | 5.0 | 6.1 | 5.4 | 6.2 | 5.8 |
| | 2.0 | 5.8 | 5.1 | 5.0 | 4.0 | 2.7 | 4.5 |
| G | 1.0 | 27.8 | 25.0 | 38.9 | 33.3 | 26.5 | 30.3 |
| | 2.0 | 32.9 | 35.0 | 35.3 | 30.1 | 30.2 | 32.7 |
| G + F | 0.5 + 0.5 | 18.9 | 17.4 | 17.3 | 23.5 | 20.5 | 19.5 |
| | 0.5 + 1.0 | 10.6 | 10.4 | 10.7 | 10.7 | 10.8 | 10.6 |
| | 1.0 + 0.5 | 20.2 | 25.5 | 21.3 | 15.7 | 23.6 | 21.3 |
| | 1.0 + 1.0 | 10.1 | 8.5 | 10.3 | 11.8 | 14.2 | 11.0 |

The rate of growth of sunflower upon the use of 2-(2,3-dihydro-2,2-dimethyl-benzofuran-7-yl-oxy)-ethyl-phosphonic acid-diethyl-ester at a rate of 1.0 and 2.0 kg./ha. was reduced similarly like by 2-chloro-ethyl-phosphonic acid. When comparing the activity of the composition with the activity of the combination of 2,2-dimethyl-2,3-dihydro-7-hydroxy-benzofuran and 2-chloro-ethyl-phosphonic acid it can be seen that the plant growth regulating activity of the new compound is stronger than the activity of the combination of the two known compounds when used at a rate of 1 kg./ha.+0.5 kg./ha. and 1 kg./ha.+1 kg./ha., respectively. The biological activity of the compound of the invention is even more significant if the comparison is performed with a combination of the starting compound at a dose of 0.5 kg./ha.+0.5 kg./ha. and 0.5 kg/ha.+1 kg./ha., respectively.

TABLE 4

Effect of pre-emergent treatment on the growth of tomato

| Treatment composition | Dose kg./ha. | Change in the % of the starting height | | | | |
|---|---|---|---|---|---|---|
| | | I. | II. | III. | IV. | Average |
| K | | 28.4 | 31.3 | 27.5 | 26.1 | 28.3 |
| Comp. No. 1 | 1.0 | 42.1 | 40.6 | 43.5 | 39.7 | 41.5 |
| | 2.0 | 27.9 | 30.8 | 31.2 | 29.3 | 29.8 |
| | 4.0 | 21.1 | 18.4 | 20.2 | 17.6 | 19.3 |
| | 8.0 | 15.1 | 13.6 | 14.5 | 12.9 | 14.0 |
| F | 2.0 | 27.5 | 26.9 | 33.1 | 28.2 | 28.9 |
| G | 2.0 | 33.1 | 32.6 | 29.8 | 32.9 | 32.1 |

When using 2-(2,3-dihydro-2,2-dimethyl-benzofuran-7-yl-oxy)-ethyl-phosphonic acid-diethyl-ester in a pre-emergent treatment the growth of tomato was significantly stimulated at a dose of 1 kg./ha. By increasing the dose the growth reducing activity of the composition could be mainly observed. At a rate of 2 kg./ha. an equilibrium state can be observed when the stimulating activity is no longer significant but the growth reducing activity cannot yet be observed.

By further increasing the dose at a rate of 4 kg./ha. the growth of tomato decreased to about ⅔ and at a rate of 8 kg./ha. to about ½.

As a further result it can be seen that 2-chloro-ethyl-phosphonic acid does not regulate the growth of the plant through the soil. The growth regulating activity of 2,2-dimethyl-2,3-dihydro-7-hydroxy-benzofuran did not reach at the tested dose the activity of 2-(2,3-dihydro-2,2-dimethyl-benzofuran-7-yl-oxy)-ethyl-phosphonic acid-diethyl-ester.

The activity of 2-(2,3-dihydro-2,2-dimethyl-benzofuran-7-yl-oxy)-ethyl-phosphonic acid-diethyl-ester upon the growth of the plants was tested by a treatment post-emergence and pre-emergence in green house tests, in culture dishes by using tomato, soybeans and sunflower as indicating plants (said plants reacting more sensitively on compounds having auxin activity).

The height of the tomato was increased by 2-(2,3-dihydro-2,2-dimethyl-benzofuran-7-yl-oxy)-ethyl-phosphonic acid-diethyl-ester and its activity can be characterized by a curve of second order in dependence on the dose.

In soybeans and sunflower the compound shows a plant growth regulating activity and when used pre-emergence 2-(2,3-dihydro-2,2-dimethyl-benzofuran-7-yl-oxy)-ethyl-phosphonic acid-diethyl-ester is absorbed from the soil through the root and acts as plant growth regulator.

Biological tests were carried out with the compound according to Example 5 i.e. 2-(4-methyl-coumarin-7-yl-oxy)-ethyl-phosphonic acid-O,O-diethyl-ester and its activity was compared with the control (K), with 2-chloro-ethyl-phosphonic acid (F) and with 7-hydroxy-4'-methyl-coumarin (M).

TABLE 5

Effect of post-emergent treatment on the growth of tomato

| Treatment | | Change in the % of the starting height | | |
|---|---|---|---|---|
| Composition | Dose kg./ha. | 4th day | 7th day | 10th day |
| K | | 29 | 53 | 71 |
| Comp. No. 5 | 0.5 | 49 | 88 | 107 |
| | 1.0 | 43 | 70 | 91 |
| | 2.0 | 34 | 62 | 81 |
| F | 0.5 | 42 | 69 | 86 |
| | 1.0 | 41 | 68 | 76 |
| | 2.0 | 43 | 65 | 70 |
| M | 0.5 | 33 | 60 | 72 |
| | 1.0 | 35 | 64 | 78 |
| | 2.0 | 37 | 70 | 82 |

The test results show that 2-(4'-methyl-coumarin-7-yl-oxy)-ethyl-phosphonic acid-O,O-diethyl-ester highly increased the growth of tomato related to the untreated control. The most significant growth stimulation was measured at the test dose of 0.5 kg./ha.

TABLE 6

Effect of post-emergent treatment on the growth of soybeans

| Treatment | | Change in the % of the starting height | | | | | |
|---|---|---|---|---|---|---|---|
| Composition | Dose kg./ha. | I. | II. | III. | IV. | V. | Average |
| K | | 23.4 | 26.9 | 21.1 | 25.1 | 26.2 | 24.5 |
| Comp. No. 5 | 0.5 | 15.1 | 16.3 | 16.0 | 15.8 | 15.0 | 15.6 |
| | 1.0 | 13.7 | 14.9 | 16.2 | 15.0 | 14.4 | 14.8 |
| | 2.0 | 13.8 | 12.6 | 14.0 | 13.0 | 14.4 | 13.6 |
| F | 0.5 | 13.0 | 11.3 | 14.1 | 15.1 | 9.4 | 12.6 |
| | 1.0 | 15.1 | 10.6 | 12.4 | 11.4 | 11.4 | 12.2 |
| | 2.0 | 6.6 | 10.0 | 8.5 | 9.5 | 8.8 | 8.7 |
| M | 0.5 | 30.7 | 31.0 | 31.5 | 33.2 | 35.4 | 32.4 |
| | 1.0 | 24.2 | 30.1 | 30.2 | 24.1 | 29.8 | 27.7 |
| | 2.0 | 21.9 | 19.0 | 20.0 | 20.2 | 18.7 | 20.0 |

The growth of the plants was approximately similarly reduced in soybeans by 2-(4'-methyl-coumarin-7-oxy)-ethyl-phosphonic-acid-O,O-diethyl-ester independently on the used active ingredient rate. The compound shows a growth reducing activity in spite of the fact that 7-hydroxy-4-methyl-coumarin at a dose of 0.5–1.0 kg./ha. stimulated the growth of soybeans.

TABLE 7

Effect of post-emergent treatment on the growth of sunflower

| Treatment | | Change in the % of the starting height | | | | | |
|---|---|---|---|---|---|---|---|
| Composition | Dose kg./ha. | I. | II. | III. | IV. | V. | Average |
| K | | 33.0 | 38.8 | 31.1 | 27.9 | 26.7 | 31.5 |
| Comp. No. 5 | 1.0 | 10.3 | 8.7 | 8.1 | 8.9 | 9.4 | 9.1 |
| | 2.0 | 8.3 | 8.0 | 8.0 | 8.4 | 8.1 | 8.2 |
| F | 1.0 | 6.3 | 5.0 | 6.1 | 5.4 | 6.2 | 5.8 |
| | 2.0 | 5.8 | 5.1 | 5.0 | 4.0 | 2.7 | 4.5 |
| M | 1.0 | 31.3 | 34.6 | 29.8 | 30.5 | 32.4 | 31.7 |
| | 2.0 | 27.4 | 28.2 | 27.5 | 26.9 | 28.1 | 27.6 |
| M + F | 0.5 + 0.5 | 20.3 | 19.8 | 21.0 | 19.5 | 20.4 | 20.2 |
| | 1.0 + 0.5 | 9.9 | 10.4 | 9.2 | 9.5 | 10.0 | 9.8 |
| | 0.5 + 1.0 | 21.4 | 25.0 | 22.0 | 21.3 | 24.2 | 22.8 |
| | 1.0 + 1.0 | 9.5 | 9.1 | 10.6 | 10.2 | 11.4 | 10.2 |

When compared with the untreated control 2-(4'-methyl-coumarin-7-yl-oxy)-ethyl-phosphonic acid-O,O-diethyl-ester reduced the growth of sunflower to about ¼. The growth reduction observed as the effect of the compound almost achieved the value measured on plants which were treated by 2-chloro-ethyl-phosphonic acid. When compared the activity of the composition with the activity of the combination of 7-hydroxy-4-methyl-coumarin and 2-chloro-ethyl-phosphonic acid it can be seen that the plant growth regulating activity of the compound is the same as when spraying on the plants together 7-hydroxy-4-methyl-coumarin at a rate of 1 kg./ha. and 2-chloro-ethyl-phosphonic acid at a rate of 0.5 kg./ha.

TABLE 8

Effect of pre-emergent treatment on the growth of tomato

| Treatment | | Change in the % of the starting height | | | | |
|---|---|---|---|---|---|---|
| Composition | Dose kg./ha. | I. | II. | III. | IV. | Average |
| K | | 28.4 | 31.3 | 27.5 | 26.1 | 28.3 |
| Comp. No. 1 | 1.0 | 43.4 | 41.2 | 40.6 | 42.8 | 42.0 |
| | 2.0 | 30.7 | 28.4 | 31.6 | 27.4 | 29.5 |
| | 4.0 | 17.33 | 16.9 | 18.7 | 18.2 | 17.8 |
| | 8.0 | 13.4 | 14.5 | 15.0 | 13.7 | 14.2 |
| F | 2.0 | 27.5 | 26.9 | 33.1 | 28.2 | 28.9 |
| M | 2.0 | 30.1 | 34.6 | 30.8 | 32.9 | 32.1 |

Upon a treatment pre-emergence with 2-(4'-methyl-coumarin-7-yl-oxy)-ethyl-phosphonic acid-O,O-diethyl-ester, the compound intensively stimulated the growth of tomato at a dose of 1 kg./ha. whereas doses 4 and 8 kg./ha. already reduced the growth of tomato.

The results further show that no plant growth regulating activity can be observed when applying 2-chloro-ethyl-phosphonic acid to the soil and when applying 7-hydroxy-4-methyl-coumarin alone the compound stimulates the growth of the plant at a moderate extent through the soil.

The growth of the indicating plants, i.e. tomato, soybeans and sunflower was tested by treatment post-emergence and pre-emergence in green house tests using culture dishes and the test compound was the compound No. 6.

The height of tomato was increased by spraying the plant with 2-(4'-methyl-coumarin-7-yl-oxy)-ethyl-phosphonic acid-diethyl-ester. The extent of plant growth was in inverse ratio to the dose. It can be further seen that the plant growth regulating activity of soybeans and sunflower under greenhouse conditions was almost similar to that of 2-chloro-ethyl-phosphonic acid.

When using 2-(4'-methyl-coumarin-7-yl-oxy)-ethyl-phosphonic acid-diethyl-ester pre-emergence the compound showed plant growth regulating activity when being absorbed through the roots from the soil.

The active ingredients according to the invention were tested post-emergence in free land tests on soybeans, on maize, on winter wheat and green paprika. The results of the tests are shown in the following tables.

SOYBEANS

Test conditions

Type of the soil: field chernozem
Green crop: sugar beet
Fertilization:
  50 kg./ha. N(ammonium-nitrate)
  100 kg./ha. $P_2O_5$ (18% superphosphate)
  120 kg./ha. $K_2O$ (50% potassium chloride)
Weed killing: 910 g./ha. 2,6-dinitro-N,N-dipropyl-4-trifluoro-methyl-aniline + 900 g./ha. N-(4-bromo-3-chloro-phenyl)-N'-methoxy-N-methyl-urea
Art: ISz-15
Stock number: 350 000 stock/ha.
parcel size: 2×10 m.
Repetition: 6
Spray-liquid: 220 l./ha.
Treatments:

| | | |
|---|---|---|
| (1) | Untreated control | |
| (2) | 2-chloro-ethyl-phosphonic acid | 250 g./ha. |
| (3) | 2-chloro-ethyl-phosphonic acid | 500 g./ha. |
| (4) | 2-chloro-ethyl-phosphonic acid | 1000 g./ha. |
| (5) | 2-(2,3-dihydro-2,2-dimethyl-benzofuran-7-yl-oxy)-ethyl-phosphonic acid-diethyl-ester | 250 g./ha. |
| (6) | 2-(2,3-dihydro-2,2-dimethyl-benzofuran-7-yl-oxy)-ethyl-phosphonic acid-diethyl-ester | 500 g./ha. |
| (7) | 2-(2,3-dihydro-2,2-dimethyl-benzofuran-7-yl-oxy)-ethyl-phosphonic acid-diethyl-ester | 1000 g./ha. |
| (8) | 2-(4-methyl-coumarin-7-yl-oxy)-ethyl-phosphonic acid-O,O—diethyl-ester | 250 g./ha. |
| (9) | 2-(4-methyl-coumarin-7-yl-oxy)-ethyl-phosphonic acid-O,O—diethyl-ester | 500 g./ha. |
| (10) | 2-(4-methyl-coumarin-7-yl-oxy)-ethyl-phosphonic acid-O,O—diethyl-ester | 1000 g./ha. |

The spraying was carried out at the beginning of the budding of the soybean. The concentration of the spray liquid was in the range of 1.13 to 4.54 g./l. related to the active ingredient. The tests were carried out using compositions disclosed in Example 5 and 10.

TABLE 9

Effect of post-emergent treatment on the crop of soybeans

| Number of treatment | Dose g./ha. | Crop average t./ha. | Change in the % of the control |
|---|---|---|---|
| 1 | — | 2.60 | 100 |
| 2 | 250 | 2.68 | 103 |
| 3 | 500 | 2.32 | 89 |
| 4 | 1000 | 2.05 | 79 |
| 5 | 250 | 2.97 | 114 |
| 6 | 500 | 2.76 | 106 |
| 7 | 1000 | 2.55 | 98 |
| 8 | 250 | 3.06 | 117 |
| 9 | 500 | 2.80 | 107 |
| 10 | 1000 | 2.61 | 100 |

The table shows that both 2-(2,3-dihydro-2,2-dimethyl-benzofuran-7-yl-oxy)-ethyl-phosphonic acid-diethyl-ester and 2-(4'-methyl-coumarin-7-yl-oxy)-ethyl-phosphonic acid-O,O-diethyl-ester increase the crop by 14–17% at a rate of 250 g./ha. By increasing the dose the crop increase decreased and at the rate of 1000 g./ha. there was already no difference.

MAIZE

Test conditions

Type of soil: field chernozem
Green crop: winter wheat
Fertilization:
  250 kg./ha. N(ammonium-nitrate)
  140 kg./ha. $P_2O_5$ (18% superphosphate)
  180 kg./ha. $K_2O$ (50% potassium chloride)
Weed killing: 2000 g./ha. N-(ethoxy-methyl)-2-ethyl-6-methyl-chloro-acetanilide + 1000 g g./ha. N-(4-bromo-3-chloro-phenyl)-N'-methoxy-N'-methyl-urea
Art: Pioneer 3709
Stock number: 82 000 stock/ha.
Parcel size: 2.1×10 m.
Repetition: 6
Spray liquid: 220 l./ha.
Treatments:

| | | |
|---|---|---|
| (1) | Untreated control | |
| (2) | 2-chloro-ethyl-phosphonic acid | 500 g./ha. |
| (3) | 2-(2,3-dihydro-2,2-dimethyl-benzofuran-7-yl-oxy)-ethyl-phosphonic acid-diethyl-ester | 250 g./ha. |
| (4) | 2-(2,3-dihydro-2,2-dimethyl-benzofuran-7-yl-oxy)-ethyl-phosphonic acid-diethyl-ester | 500 g./ha. |
| (5) | 2-(2,3-dihydro-2,2-dimethyl-benzofuran-7-yl-oxy)-ethyl-phosphonic acid-diethyl-ester | 1000 g./ha. |
| (6) | 2-(4'-methyl-coumarin-7-yl-oxy)-ethyl-phosphonic acid-O,O—diethyl-ester (compound according to Example 5) | 250 g./ha. |

| | -continued | |
|---|---|---|
| (7) | 2-(4'-methyl-coumarin-7-yl-oxy)-ethyl-phosphonic acid-O,O—diethyl-ester | 500 g./ha. |
| (8) | 2-(4'-methyl-coumarin-7-yl-oxy)-ethyl-phosphonic acid-O,O—diethyl-ester | 1000 g./ha. |

The treatments were carried out on maize at a development stage of 6–8 leaves, concentration of the spray liquid related to the active ingredient changed in the range of 1.13 to 4.54 g./l. The tests were carried out by using compositions disclosed in Examples 5 and 10.

TABLE 10

Effect of post-emergent treatment on the crop of maize

| Number of treatment | Dose g./ha. | Crop average t./ha. | Change in the % of the control |
|---|---|---|---|
| 1 | — | 7.12 | 100 |
| 2 | 500 | 5.68 | 80 |
| 3 | 250 | 8.20 | 115 |
| 4 | 500 | 8.48 | 119 |
| 5 | 1000 | 8.38 | 117 |
| 6 | 250 | 8.31 | 116 |
| 7 | 500 | 8.43 | 118 |
| 8 | 1000 | 8.22 | 115 |

In maize the compounds of the invention increase the crop by 15–19% independently on the dose. 2-Chloro-ethyl-phosphonic acid reduced the crop by 20% at a dose of 500 g./ha. as opposed to the compounds of the invention.

WINTER WHEAT

Test conditions

Type of soil: field chernozem
Green crop: green peas
Fertilization:
  200 kg./ha. N(ammonum nitrate)
  120 kg./ha. P$_2$O$_5$ (18% superphosphate)
  140 kg./ha. K$_2$O (50% potassium chloride)
Weed killing: 1000 g./ha. of ammonium salt of 2,4-dichloro-phenoxy-acetic acid
Art: MV-8
Stock number: 5.5 million stock/ha.
Parcel size: 2×10 m.
Repetition: 6
Spray liquid: 220 l./ha.
Treatments:

| | | |
|---|---|---|
| (1) | Untreated control | |
| (2) | 2-chloro-ethyl-phosphonic acid | 500 g./ha |
| (3) | 2-chloro-ethyl-phosphonic acid | 1000 g./ha. |
| (4) | 2-chloro-ethyl-phosphonic acid | 2000 g./ha. |
| (5) | 2-(2,3-dihydro-2,2-di-methyl-benzofuran-7-yl-oxy)-ethyl-diethyl-ester | 500 g./ha. |
| (6) | 2-(2,3-dihydro-2,2-di-methyl-benzofuran-7-yl-oxy)-ethyl-diethyl-ester | 1000 g./ha. |
| (7) | 2-(2,3-dihydro-2,2-di-methyl-benzofuran-7-yl-oxy)-ethyl-diethyl-ester | 2000 g./ha. |
| (8) | 2-(4'-methyl-coumarin-7-yl-oxy)-ethyl-phosphonic acid-O,O—diethyl-ester | 500 g./ha. |
| (9) | 2-(4'-methyl-coumarin-7-yl-oxy)-ethyl-phosphonic acid-O,O—diethyl-ester | 1000 g./ha. |
| (10) | 2-(4'-methyl-coumarin-7-yl-oxy)-ethyl-phosphonic acid-O,O—diethyl-ester | 2000 g./ha. |
| (11) | 2-chloro-ethyl-phosphonic acid | 50 g./ha. |
| (12) | 2-chloro-ethyl-phosphonic acid | 100 g./ha. |
| (13) | 2-chloro-ethyl-phosphonic acid | 200 g./ha. |
| (14) | 2-(2,3-dihydro-2,2-dimethyl-benzofuran-7-yl-oxy)-ethyl-phosphonic acid-diethyl-ester | 50 g./ha. |
| (15) | 2-(2,3-dihydro-2,2-dimethyl-benzofuran-7-yl-oxy)-ethyl-phosphonic acid-diethyl-ester | 100 g./ha. |
| (16) | 2-(2,3-dihydro-2,2-dimethyl-benzofuran-7-yl-oxy)-ethyl-phosphonic acid-diethyl-ester | 200 g./ha. |
| (17) | 2-(4'-methyl-coumarin-7-yl-oxy)-ethyl-phosphonic acid-O,O—diethyl-ester | 50 g./ha. |
| (18) | 2-(4'methyl-coumarin-7-yl-oxy)-ethyl-phosphonic acid-O,O—diethyl-ester | 100 g./ha. |
| (19) | 2-(4'-methyl-coumarin -7-yl-oxy)-ethyl-phosphonic acid-O,O—diethyl-ester | 200 g./ha. |

Treatments No. 2 to 10 were performed during growing thick and treatments No. 11 to 19 were performed during earing. The spray liquid concentration changed in the range of 0.22 to 9.1 g./l. related to the active ingredient. Compositions disclosed in Examples 6 and 11 were used.

TABLE 11

Effect of post-emergent treatments on the crop of winter wheat

| Number of treatment | Dose g./ha. | Crop average t./ha. | Change in the % of the control |
|---|---|---|---|
| 1 | — | 7.75 | 100 |
| 2 | 400 | 7.82 | 101 |
| 3 | 1000 | 7.53 | 97 |
| 4 | 2000 | 6.79 | 87 |
| 5 | 500 | 8.66 | 112 |
| 6 | 1000 | 8.51 | 110 |
| 7 | 2000 | 8.46 | 109 |
| 8 | 500 | 8.88 | 115 |
| 9 | 1000 | 8.97 | 116 |
| 10 | 2000 | 8.80 | 114 |
| 11 | 50 | 7.74 | 100 |
| 12 | 100 | 7.88 | 102 |
| 13 | 200 | 7.44 | 96 |
| 14 | 50 | 7.79 | 100 |
| 15 | 100 | 8.26 | 106 |
| 16 | 200 | 8.40 | 108 |
| 17 | 50 | 7.83 | 101 |
| 18 | 100 | 8.47 | 109 |
| 19 | 200 | 8.35 | 107 |

In winter wheat the compounds of the invention increase the crop by 9–16% during the treatments performed when growing thick.

Upon the effect of 2-(2,3-dihydro-2,2-dimethyl-benzofuran-7-yl-oxy)-ethyl-phosphonic acid-diethyl-ester the crop was increased by 9–12% and upon the treatment with 2-(4'-methyl-coumarin-7-yl-oxy)-ethyl-phosphonic-acid-O,O-diethyl-ester the crop increased by 14–16%. When performing the test during earing the crop increase was somewhat lower at a rate of 100–200 g./ha. 6–9% crop increase was achieved.

RED PEPPER

Test conditions

Type of soil: field chernozem
Green crop: onion
Fertilization: 40 t./ha. organic fertilizer
Weed killing: 310 g./ha. 2,6-dinitro-N,N-dipropyl-4-trifluoro-methyl-aniline and manual hoeing
Art: Szeged spicy F 03 red pepper
Stock number: 365 000 stock/ha.
Parcel size: 2×10 m.
Repetition: 6
Spray liquid: 220 l./ha.
Treatments:

| | |
|---|---|
| (1) Untreated control | |
| (2) 2-chloro-ethyl-phosphonic acid | 1000 g./ha. |
| (3) 2-(2,3-dihydro-2,2-dimethyl-benzofuran-7-yl-oxy)-ethyl-phosphonic acid-diethyl-ester | 1000 g./ha. |
| (4) 2-(4-methyl-coumarin-7-yl-oxy)-ethyl-phosphonic acid-O,O—diethyl-ester | 1000 g./ha. |

The spraying was performed at the beginning of the colourization of the pepper. The spray liquid concentration was 4.54 g./l. related to the active ingredient. Compositions disclosed in Examples 6 and 11 were used.

TABLE 12

Effect of post-emergent treatments on the crop of red pepper and its qualitative parameters

| Number of treatment and compositions | Crop t./ha. | Crop T | Ratio of green peppers % | Dye T | Colour distribution of ripe peppers % Completely ripe | Half ripe | Worthless |
|---|---|---|---|---|---|---|---|
| 1 | 3.15 | 100 | 28 | 8.84 | 42.5 | 22.6 | 34.8 |
| 2 | 2.85 | 90 | 25 | 10.07 | 51.2 | 28.4 | 20.4 |
| 3 | 3.60 | 114 | 20 | 9.68 | 72.0 | 10.0 | 18.0 |
| 4 | 3.69 | 117 | 19 | 9.85 | 69.8 | 11.6 | 19.6 |

The crop increased by 14–17% on red-pepper parcels treated with the compound of the invention. The ratio of the uncoloured peppers also decreased to 19–20% from the value of the untreated control 28% and the dye % of the coloured peppers increased. The ratio of the completely coloured peppers was higher and the amount of half ripe and worthless brown peppers significantly decreased.

We claim:

1. Etherified hydroxy-alkyl-phosphonic acid derivatives of the general formula (I)

$$R-O-CH_2-CH_2-\overset{\overset{O}{\|}}{P}\overset{OR^1(Me)}{\underset{OR^2}{\diagdown}} \quad (I)$$

wherein
R stands for 2,3-dihydro-2,2-dimethyl-benzofuran-7-yl, 4-methyl-coumarin-7-yl, 2,2,4-trimethyl-(2H)-chromen-5-yl or 2,2,4-trimethyl-(2H)-chromen-7-yl,
$R^1$ and $R^2$ are the same or different and stand for hydrogen, $C_{1-8}$ alkyl, $C_{1-4}$ halogen-alkyl, $C_{1-4}$ alkoxy-$C_{1-2}$-alkyl, Me stands for a monovalent cation and represents the salt of the acid.

2. 2-(2,3-dihydro-2,2-dimethyl-benzofuran-7-yl-oxy)--ethyl-phosphonic acid-diethyl-ester.

3. 2-(2',4',4-trimethyl-(2H)-chromen-7-yl-oxy)-ethyl-phosphonic acid-diethyl-ester.

4. 2-(4'-methyl-coumarin-7-yl-oxy)-ethyl-phosphonic acid-O,O-diethyl-ester.

5. Plant growth regulating agent comprising as active ingredient 0.5–95% by mass of an etherified hydroxyalkyl-phosphonic acid derivative of the general formula (I) of claim 1 wherein
R stands for 2,3-dihydro-2,2-dimethyl-benzofuran-7-yl, 4-methyl-courmarin-7-yl, 2,2,4-trimethyl-(2H)-chromen-5-yl or 2,2,4-trimethyl-(2H)-chromen-7-yl,
$R^1$ and $R^2$ are the same or different and stand for hydrogen, $C_{1-8}$ alkyl, $C_{1-4}$ halogen-alkyl, $C_{1-4}$ alkoxy-$C_{1-2}$ alkyl, Me a monovalent cation,
admixed with the usual solid and/or liquid carriers and optionally surfactants.

6. Method of treatment of plants pre or post emergence comprising applying an effective amount of a compound of the general formula (I) as claimed in claim 1 to the plants or its surroundings.

* * * * *